US005480990A

United States Patent [19]
Kiefer et al.

[11] Patent Number: 5,480,990
[45] Date of Patent: Jan. 2, 1996

[54] BICYCLOPOLYAZAMACROCYCLO-CARBOXYLIC ACID COMPLEXES FOR USE AS CONTRAST AGENTS

[75] Inventors: Garry E. Kiefer, Lake Jackson; Jaime Simon, Angleton, both of Tex.

[73] Assignee: The Dow Chemical Company, Midland, Mich.

[21] Appl. No.: 171,587

[22] Filed: Dec. 22, 1993

Related U.S. Application Data

[60] Continuation-in-part of Ser. No. 141,842, Oct. 22, 1993, which is a division of Ser. No. 805,270, Dec. 10, 1991, abandoned.

[51] Int. Cl.$^6$ .......................... C07F 9/652; A61K 31/555
[52] U.S. Cl. ................. 540/465; 540/472; 530/391.3; 530/391.5; 424/9.34; 424/9.35
[58] Field of Search ..................... 540/465, 472

[56] References Cited

U.S. PATENT DOCUMENTS

| | | | |
|---|---|---|---|
| 4,156,683 | 5/1979 | Lehn | 260/338 |
| 4,639,365 | 1/1987 | Sherry | 424/9 |
| 4,647,447 | 3/1987 | Gries et al. | 424/9 |
| 4,822,594 | 4/1989 | Gibby | 424/9 |
| 4,877,600 | 10/1989 | Bonnemain et al. | 424/4 |
| 4,885,363 | 12/1989 | Tweedle et al. | 540/465 |
| 4,889,931 | 12/1989 | Rocklage et al. | 540/465 |
| 4,920,195 | 4/1990 | Kankare et al. | 534/16 |
| 4,923,985 | 5/1990 | Gansow et al. | 540/474 |
| 4,933,441 | 6/1990 | Gibby | 536/112 |
| 4,940,796 | 7/1990 | Mathias et al. | 546/323 |
| 4,957,939 | 9/1990 | Gries et al. | 514/442 |
| 4,963,344 | 10/1990 | Gries et al. | 424/9 |
| 4,986,980 | 1/1991 | Jacobsen | 429/9 |
| 5,026,802 | 6/1991 | Mathias et al. | 526/259 |
| 5,047,527 | 9/1991 | Handel et al. | 540/474 |
| 5,049,667 | 9/1991 | Schafer et al. | 540/474 |
| 5,053,503 | 10/1991 | Dean et al. | 540/474 |
| 5,334,371 | 8/1994 | Gries et al. | 540/465 |

FOREIGN PATENT DOCUMENTS

| | | | |
|---|---|---|---|
| 0238196 | 9/1987 | European Pat. Off. | 540/465 |
| 0298933 | 1/1989 | European Pat. Off. | 546/393 |
| 0352218 | 1/1990 | European Pat. Off. | 540/465 |
| 0391766 | 10/1990 | European Pat. Off. | 540/465 |
| 0438206 | 7/1991 | European Pat. Off. | 540/465 |

OTHER PUBLICATIONS

Chemical Abstracts, vol. 74, (1974), p. 399, abstract No. 60361f.
Chemical Abstracts, vol. 85, (1976), p. 399, abstract No. 198997b.
Chemical Abstracts, vol. 95, (1981), pp. 702, abstract No. 115487t.
Chemical Abstracts, vol. 100, (1984), p. 593, abstract No. 209772f.
Chemical Abstracts, vol. 109, (1988), p. 839, abstract No. 242975h.
Chemical Abstracts, vol. 110, (1989), p. 892, abstract No. 127400a.
Chemical Abstracts, vol. 111, (1989), p. 921, abstract No. 208180b.
Chemical Abstracts, vol. 113, (1990), p. 701, abstract No. 59139g.
Chemical Abstracts, vol. 115, (1991), p. 21, abstract No. 280870b.
Chemical Abstracts, vol. 115, (1991) p. 585, abstract No. 58294h.
Chemical Abstracts, vol. 115, (1991), p. 845, abstract No. 20829y.
Chemical Abstracts, vol. 115 (1991), p. 938, abstract No. 183387s.
Chemical Abstracts, vol. 116, (1992), p. 583, abstract No. 21083h.
Derwint Publications, Ltd., abstract No. 85–018012/03, 25 Mar. 1983.
Derwint Publications, Ltd., abstract No. 87–250202/35, Feb. 13, 1986.
Derwint Publications, Ltd., abstract No. 89–206577/28, Dec. 24, 1987.
Derwint Publications, Ltd., abstract No. 89–370686/50, May 25, 1988.
Derwint Publications, Ltd., abstract No. 90–099224/13, Aug. 24, 1988.
Derwint Publications, Ltd., abstract No. 91–216892/30, Jan. 18, 1990.
Derwint Abstract No. 91–283191/39 for EP 448191 n.d.
Derwint Abstract No. 91–304859/42 for EP 451824 n.d.
Derwint Abstract No. 91–319187/44 for EP 454078 n.d.
On Line Reference Form IFI Claims Database for US 5,053,503 n.d.
On Line reference Form IFI Claims Database for US 5,049,667 n.d.
Tetrahedron, vol. 37, pp. 767–772, (1981) Stetter et al.

*Primary Examiner*—Robert T. Bond
*Attorney, Agent, or Firm*—Karen L. Kimble

[57] ABSTRACT

Complexes of bicyclopolyazamacrocyclocarboxylic acid with Gd, Mn or Fe ions are disclosed. The complexes can be covalently attached to a biologically active molecule, e.g. an antibody or antibody fragment, to form conjugates. The complexes and conjugates are useful as contrast agents for diagnostic purposes.

11 Claims, No Drawings

5,480,990

BICYCLOPOLYAZAMACROCYCLO-CARBOXYLIC ACID COMPLEXES FOR USE AS CONTRAST AGENTS

CROSS REFERENCE TO RELATED APPLICATIONS

This application is a continuation-in-part of our co-pending application Ser. No. 08/141,842, filed Oct. 22, 1993, now pending, which is a divisional of Ser. No. 07/805,270 filed Dec. 10, 1991, now abandoned. All of these prior application documents are hereby incorporated by reference.

FIELD OF THE INVENTION

This invention concerns complexes that contain as the ligand bicyclopolyazamacrocyclocarboxylic acids, and conjugates thereof, for use as contrast agents in magnetic resonance imagine (MRI). Processes for preparing these complexes and conjugates are also provided. To better understand this invention, a brief background on MRI is provided in the following section.

BACKGROUND OF THE INVENTION

MRI is a non-invasive diagnostic technique which produces well resolved cross-sectional images of soft tissue within an animal body, preferably a human body. This technique is based upon the property of certain atomic nuclei (e.g. water protons) which possess a magnetic moment [as defined by mathematical equations; see G. M. Barrow, *Physical Chemistry*, 3rd Ed., McGraw-Hill, New York (1973)] to align in an applied magnetic field. Once aligned, this equilibrium state can be perturbed by applying an external radio frequency (RF) pulse which causes the protons to be tilted out of alignment with the magnetic field. When the RF pulse is terminated, the nuclei return to their equilibrium state and the time required for this return to occur is known as the relaxation time. The relaxation time consists of two parameters known as spin-lattice (T1) and spin-spin (T2) relaxation and it is these relaxation measurements which give information on the degree of molecular organization and interaction of protons with the surrounding environment.

Since water content of living tissue is substantial and variations in content and environment exist among tissue types, diagnostic images of biological organisms are obtained which reflect proton density and relaxation times. The greater the differences in relaxation times (T1 and T2) of protons present in tissue being examined, the greater will be the contrast in the obtained image [*J. Magnetic Resonance* 33, 83–106 (1979)].

It is known that paramagnetic chelates possessing a symmetric electronic ground state can dramatically affect the T1 and T2 relaxation rates of juxtaposed water protons and that the effectiveness of the chelate in this regard is related, in part, to the number of unpaired electrons producing the magnetic moment [*Magnetic Resonance Annual* 231–266 (Raven Press, New York (1985)]. It has also been shown that when a paramagnetic chelate of this type is administered to a living animal, its effect on the T1 and T2 of various tissues can be directly observed in the magnetic resonance (MR) images with increased contrast being observed in the areas of chelate localization. It has therefore been proposed that stable, non-toxic paramagnetic chelates be administered to animals in order to increase the diagnostic information obtained by MRI [*Frontiers of Biol. Energetics I*, 752–759 (1978); *J. Nucl. Med.* 25, 506–513 (1984); *Proc. of NMR Imaging Symp.* (Oct. 26– 27, 1980); F. A. Cotton et al., *Adv. Inorg. Chem.* 634–639 (1966)]. Paramagnetic metal chelates used in this manner are referred to as contrast enhancement agents or contrast agents.

There are a number of paramagnetic metal ions which can be considered when undertaking the design of an MRI contrast agent. In practice, however, the most useful paramagnetic metal ions are gadolinium ($Gd^{+3}$), iron ($Fe^{+3}$), manganese ($Mn^{+2}$) and ($Mn^{+3}$), and chromium ($Cr^{+3}$), because these ions exert the greatest effect on water protons by virtue of their large magnetic moments. In a non-complexed form (e.g. $GdCl_3$), these metal ions are toxic to an animal, thereby precluding their use in the simple salt form. Therefore, a fundamental role of the organic chelating agent (also referred to as a ligand) is to render the paramagnetic metal non-toxic to the animal while preserving its desirable influence on $T_1$ and T2 relaxation rates of the surrounding water protons.

Art in the MRI field is quite extensive, such that the following summary, not intended to be exhaustive, is provided only as a review of this area and other compounds that are possibly similar in structure. U.S. Pat. No. 4,899,755 discloses a method of alternating the proton NMR relaxation times in the liver or bile duct of an animal using $Fe^{+3}$-ethylene-bis(2 -hydroxyphenylglycine) complexes and its derivatives, and suggests among various other compounds the possible use of a pyridine macrocyclomethylenecarboxylic acid. U.S. Pat. No. 4,880,008 (a CIP of U.S. Pat. No. 4,899,755) discloses additional imaging data for liver tissue of rats, but without any additional complexes being shown. U.S. Pat. No. 4,980,148 discloses gadolinium complexes for MRI which are non-cyclic compounds. C. J. Broan et al., *J. Chem. Soc., Chem. Commun.*, 1739–1741 (1990) describe some bifunctional macrocyclic phosphinic acid compounds. C. J. Broan et al., *J. Chem. Soc..Chem. Commun.*, 1738–1739 (1990) describe compounds that are triazabicyclo compounds. I. K. Adzamli et al., *J. Med. Chem.* 32, 139–144 (1989) describes acyclic phosphonate derivatives of gadolinium complexes for NMR imaging.

At the present time, the only commercial contrast agent available in the U.S. is the complex of gadolinium with diethylenetriaminepentaacetic acid (DTPA-$Gd^+$- Magnevist™ by Shering). Magnevist™ is considered as a non-specific/perfusion agent since it freely distributes in extracellular fluid, followed by efficient elimination through the renal system. Magnevist™ has proven to be extremely valuable in the diagnosis of brain lesions since the accompanying breakdown of the blood/brain barrier allows perfusion of the contrast agent into the affected regions. In addition to Magnevist™, Guerbet is commercially marketing a macrocyclic perfusion agent (Dotarem™) which presently is only available in Europe. A number of other potential contrast agents are in various stages of development.

SUMMARY OF THE INVENTION

The present invention is directed to novel complexes comprising a ligand that is a bicyclopolyazamacrocyclocarboxylic acid of the formula

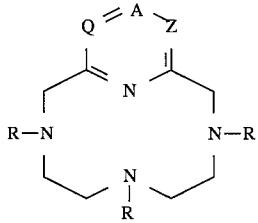

wherein:
R is

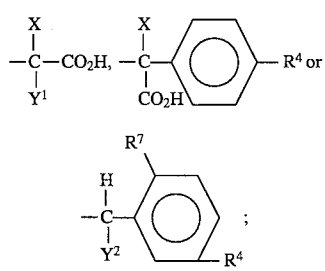

where:
X and $Y^1$ are independently H, OH, $C_1$–$C_3$ alkyl;
Y2 is H or COOH;
$R^7$ is H, OH or $OCH_3$; and
$R^4$ is H, $NO_2$, $NH_2$, isothiocyanato, semicarbazido, thiosemicarbazido, maleimido, bromoacetamido or carboxyl;
with the proviso that at least two R terms must be

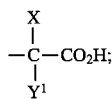

A=CH, N, C—Br, C—Cl, C—$OR^1$ C—$OR^2$, $N^+$—$R^3$ $X^-$, or

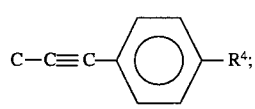

where:
$R^1$=H, $C_1$–$C_5$ alkyl, benzyl, or benzyl substituted with at least one $R^4$;
$R^2$ is $C_1$–$C_{16}$ alkylamino;
$R^3$ is $C_1$–$C_{16}$ alkyl, benzyl, or benzyl substituted with at least one $R^4$;
$R^4$ is defined as before;
$X^-$ is $Cl^-$, $Br^-$, $I^-$ or $H_3CCO_2^-$;
Q and Z independently are CH, N, N+—$R^3$ $X^-$, C—$CH_2$—$OR^1$ or C—C(O)—$R^5$;
where:
$R^1$ and $R^3$ are defined as above;

$R^5$ is —O—($C_1$–$C_3$ alkyl), OH or $NHR^6$;
$R^6$ is $C_1$–$C_5$ alkyl or a biologically active material;
$X^-$ is defined as above; and
with the proviso that:
a) when Q, A or Z is N or $N^+$—$R^3$ $X^-$, then the other two groups must be CH;
b) when A is C—Br, C—Cl, C—$OR^1$ or C—$OR^2$ then both Q and Z must be CH;
c) the sum of the $R^2$, $R^4$ and $R^6$ terms may not exceed one, and one of $R^2$, $R^4$ or $R^6$ must be present; and
d) only one of Q or Z can be C—C(O)—$R^5$ and when one of Q or Z is C—C(O)—$R^5$, then A must be CH; and
complexed with a metal ion selected from $Gd^{+3}$, $Mn^{+2}$ or $Fe^{+3}$; or
pharmaceutically-acceptable salts thereof.

Bifunctional complexes of Formula (I) are desirable to prepare the conjugates of this invention. Such ligands must have at least one of $R^2$, $R^4$ or $R^6$ present:
one R term is

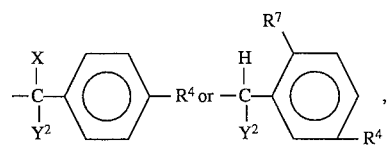

where
X, y2 $R^4$ and $R^7$ are defined as above; or
A is C—$OR^1$, C—$OR^2$, where $R^1$ and $R^2$ are defined as above or

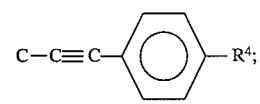

where
$R^4$ is defined as above; or
A is CH, and one of Q or Z is CH and the other is C—C(O)—$R^5$ or C—$CH_2$—$OR^1$, where $R^1$ and $R^5$ are defined as above;
preferred are those ligands where $R^5$ is $NHR^6$, where $R^6$ is a biologically active material.

The ligands of Formula (I) are complexed with various metal ions, such as gadolinium ($Gd^{+3}$), iron ($Fe^{+3}$), and manganese ($Mn^{+2}$), and $Gd^+$ being preferred. The complexes so formed can be used by themselves or can be attached, by being covalently bonded, to a larger molecule, such as a dextran, a polypeptide or a biologically active molecule, including an antibody or fragment thereof, and used for diagnostic purposes. Such conjugates and complexes are useful as contrast agents.

It would be advantageous if contrast agents were developed that could have site specificity for the tissue desired to be imaged, rather than non-specific/perfusion agents. The complexes and conjugates of this invention can be modified to provide a specific overall charge. For example, when the metal ion is +3 the following can be obtained:

(A) an overall neutral charge—when R is

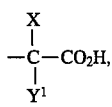

and X and $Y^1$ are all equal to H;

(B) an overall +1 charge—when one of A, Q or Z is $N^+$—$R^3$ $X^-$, where $R^3$ and $X^-$ are defined as above; and the three R terms are

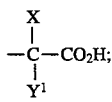

and X and $Y_1$ are all equal to H.

Both the complexes and conjugates may be formulated to be in a pharmaceutically acceptable form for administration to an animal.

Use of the ligands of this invention with other metal ions for diagnosis of disease states such as cancer is possible. The use of those complexes and conjugates is discussed in copending U.S. patent application Ser. No. 07/805,392, filed Dec. 10, 1991, and entitled "Bicyclopolyazamacrocyclocarboxylic Acid Complexes, and Conjugates Thereof, for Use as Radiopharmaceuticals" by G. E. Kiefer and J. Simon (Attorney Docket No. C-40,356), filed on even date herewith, the disclosure of which is hereby incorporated by reference.

DETAILED DESCRIPTION OF THE INVENTION

The complex has the ligand of Formula (I) numbered for nomenclature purposes as follows:

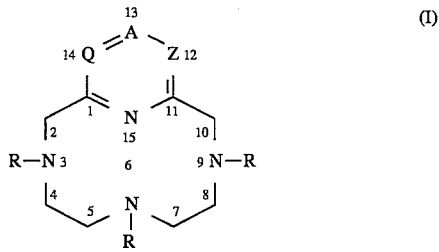

The present invention concerns development of contrast agents having a neutral or +1 charge which enables site specific delivery of the contrast agent to a desired tissue. The advantage being increased contrast in the areas of interest based upon tissue affinity as opposed to contrast arising from non-specific perfusion which may or may not be apparent with an extracellular agent. The specificity of the ligand of Formula (I) may be controlled by adjusting the total charge and lipophilic character of the complex. The overall range of the charge of the complex is from +1 to 0. For example, for a complex having a +1 overall charge has heart uptake expected; whereas when the overall charge of the complex is 0 (thus neutral), the complex may have the ability to cross the blood brain barrier and normal brain uptake may be possible.

Tissue specificity may also be realized by ionic or covalent attachment of the chelate to a naturally occurring or synthetic macromolecule having specificity for a desired target tissue. One possible application of this approach is through the use of chelate conjugated monoclonal antibodies which would transport the paramagnetic chelate to diseased tissue enabling visualization by MRI. In addition, attachment of a paramagnetic chelate to a macromolecule can further increase the contrast agent efficiency resulting in improved contrast relative to the unbound chelate. Recent work by Lauffer (U.S. Pat. Nos. 4,880,008 and 4,899,755) has demonstrated that variations in lipophilicity can result in tissue-specific agents and that increased lipophilic character favors non-covalent interactions with blood proteins resulting in enhancement of relaxivity.

Additionally, the present contrast agents of Formula (I) which are neutral in charge are particularly preferred for forming the conjugates of this invention since undesirable ionic interactions between the chelate and protein are minimized which preserves the antibody immunoreactivity. Also the present neutral complexes reduce the osmolarity relative to DTPA-$Gd^{+3}$, which may alleviate the discomfort of injection.

While not wishing to be bound by theory, it is believed that when a charged complex of the invention is made (e.g. +1 for heart), the variations in that chelate ionic charge can influence biolocalization. Thus, if the antibody or other directing moiety is also specific for the same site, then the conjugate displays two portions to aid in site specific delivery.

The terms used in Formula (I) and for this invention are further defined as follows. "$C_1$–$C_3$ alkyl", "$C_1$–$C_5$ alkyl", "$C_1$–$C_{18}$ alkyl", include both straight and branched chain alkyl groups. An "animal" includes a warmblooded mammal, preferably a human being.

"Biologically active material" refers to, for example, a dextran, peptide, or molecules that have specific affinity for a receptor, or preferably antibodies or antibody fragments.

"Antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "radioactive metal chelate/antibody conjugate" or "conjugate", the "antibody" is meant to include whole antibodies and/or antibody fragments, including semisynthetic or genetically engineered variants thereof. Possible antibodies are 1116-NS-19-9 (anti-colorectal carcinoma), 1116-NS-3d (anti-CEA), 703D4 (anti-human lung cancer), 704A1 (anti-human lung cancer), $CC_{49}$ (anti-TAG-72), $CC_{83}$ (anti-TAG-72) and B72.3. The hybridoma cell lines 1116-NS-19-9, 1116-NS-3d, 703D4, 704A1, $CC_{49}$, $CC_{83}$ and B72.3 are deposited with the American Type Culture Collection, having the accession numbers ATCC HB 8059, ATCC CRL 8019, ATCC HB 8301, ATCC HB 8302, ATCC HB 9459, ATCC HB 9453 and ATCC HB 8108, respectively.

As used herein, "complex" refers to a complex of the compound of the invention, e.g. Formula (I), complexed with a metal ion, where at least one metal atom is chelated or sequestered: "conjugate" refers to a metal ion chelate that is covalently attached to an antibody or antibody fragment. The terms "bifunctional coordinator", "bifunctional chelating agent" and "functionalized chelant" are used interchangeably and refer to compounds that have a chelant moiety capable of chelating a metal ion and a moiety covalently bonded to the chelant moiety that is capable of serving as a means to covalently attach to an antibody or antibody fragment.

The bifunctional chelating agents described herein (represented by Formula I) can be used to chelate or sequester the metal ions so as to form metal ion chelates (also referred to herein as "complexes"). The complexes, because of the presence of the functionalizing moiety (represented by $R^2$, $R^4$ or $R^6$ in Formula I), can be covalently attached to biologically active materials, such as dextran, molecules that have specific affinity for a receptor, or preferably covalently attached to antibodies or antibody fragments. Thus the complexes described herein may be covalently attached to an antibody or antibody fragment or have specific affinity for a receptor and are referred to herein as "conjugates".

As used herein, "pharmaceutically-acceptable salt" means any salt or mixtures of salts of a complex or conjugate of formula (I) which is sufficiently non-toxic to be useful in therapy or diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic,

DETAILED DESCRIPTION OF THE PROCESS

The complexes or conjugates of the present invention contain a ligand of Formula (I). The ligands are prepared by various processes. Typical general synthetic approaches to such processes are provided by the reaction schemes given below.

In Scheme 1, the compounds of Formula (I) are prepared wherein Q, A and Z=CH, and all three R=

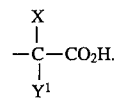

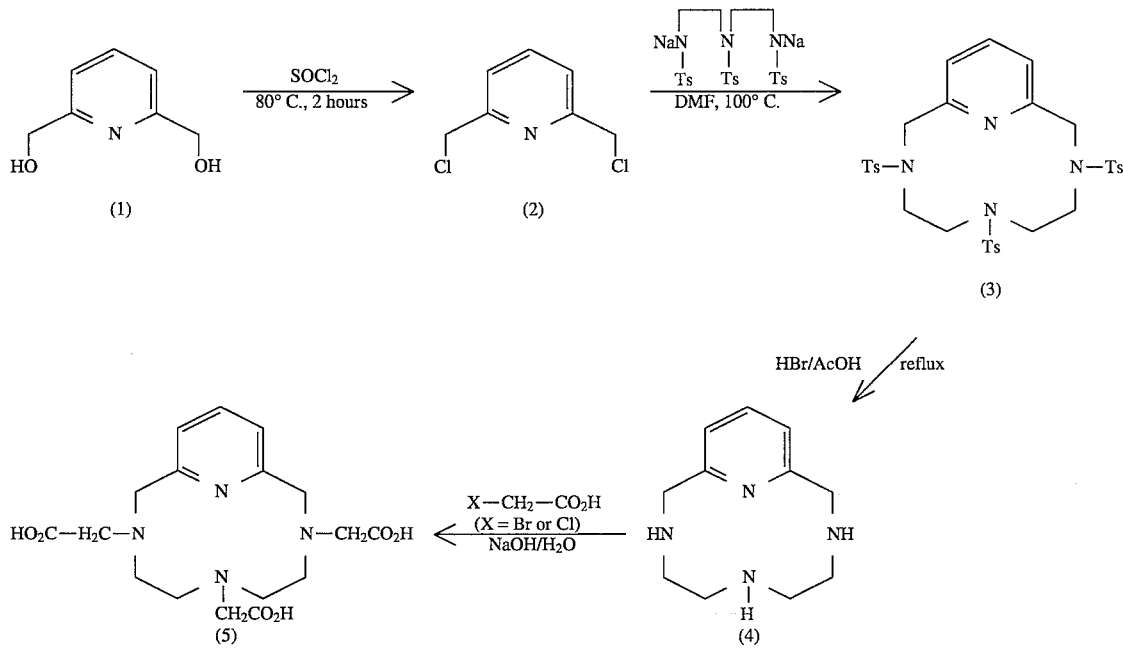

a compound of Formula (I)

glutamic, gluconic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the complexes or conjugates of formula (I) where the salt is potassium, sodium or ammonium. Also included are mixtures of the above salts.

Scheme 2 prepares the compounds of Formula (I) wherein A=C—Br, and Q and Z=CH.
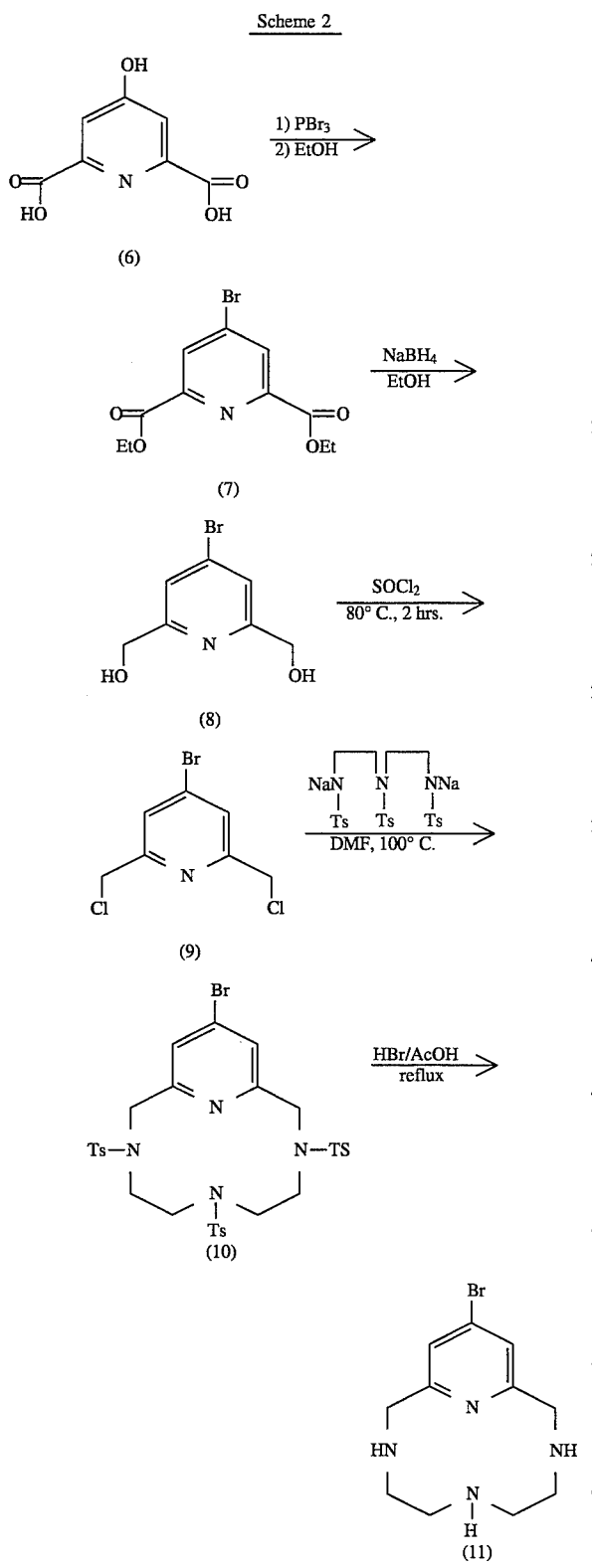
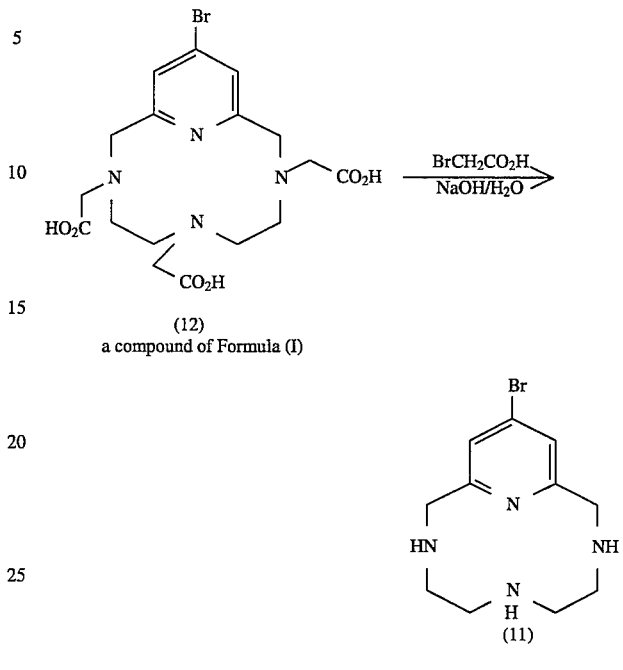
Scheme 3 prepares the compounds of Formula (I) wherein A=
$$C-C \equiv C-\phantom{}\!\!\!\!\!\!\bigcirc\!\!\!\!\!\!\phantom{}-R^4;$$
$R^4$=H, $NO_2$, $NH_2$ or SCN; and Q and Z=CH.
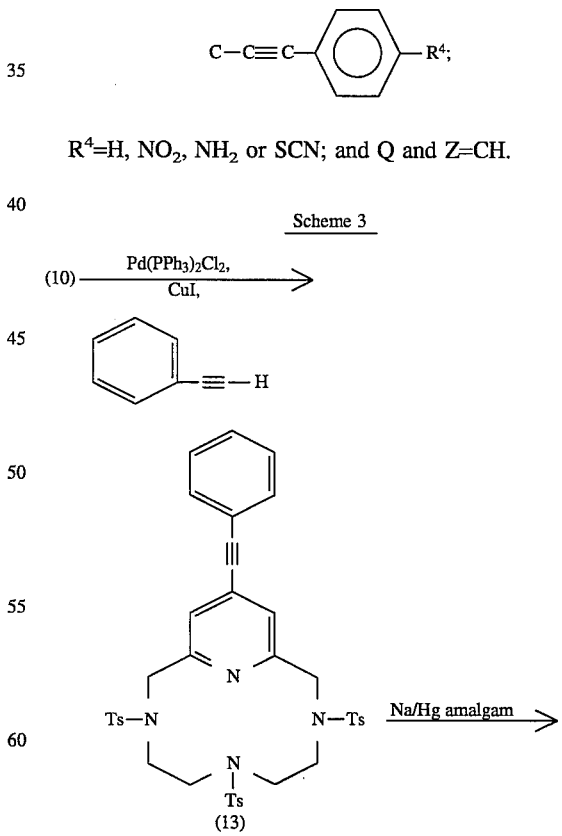

-continued
Scheme 3
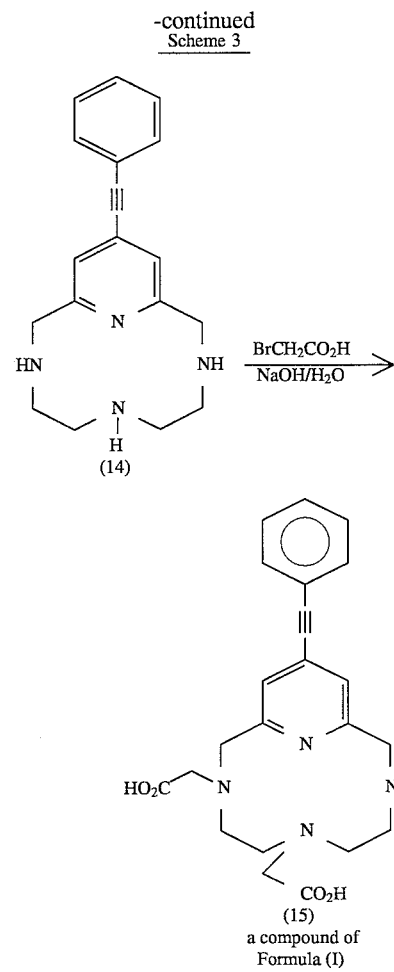
Scheme 4 prepares the compounds of Formula (I) wherein A=C—OR² where R²=C₁–C₅ alkylamino; and Q and Z=CH.
Scheme 4
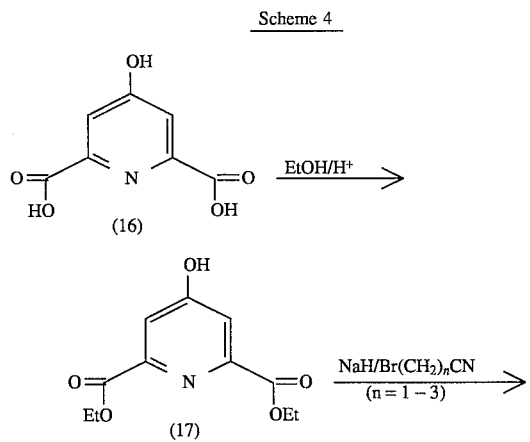
-continued
Scheme 4
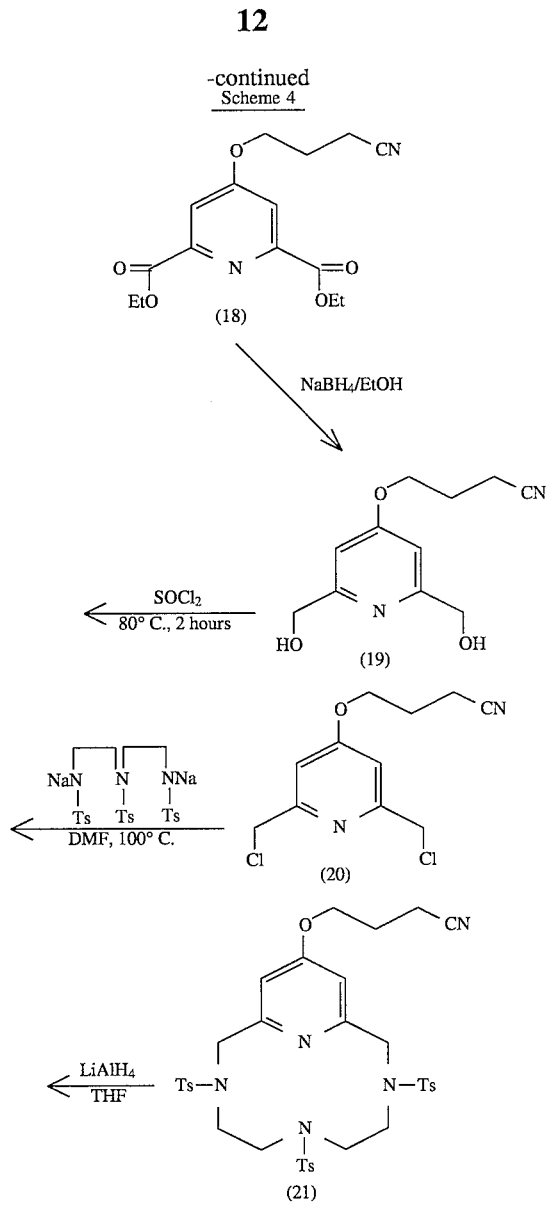

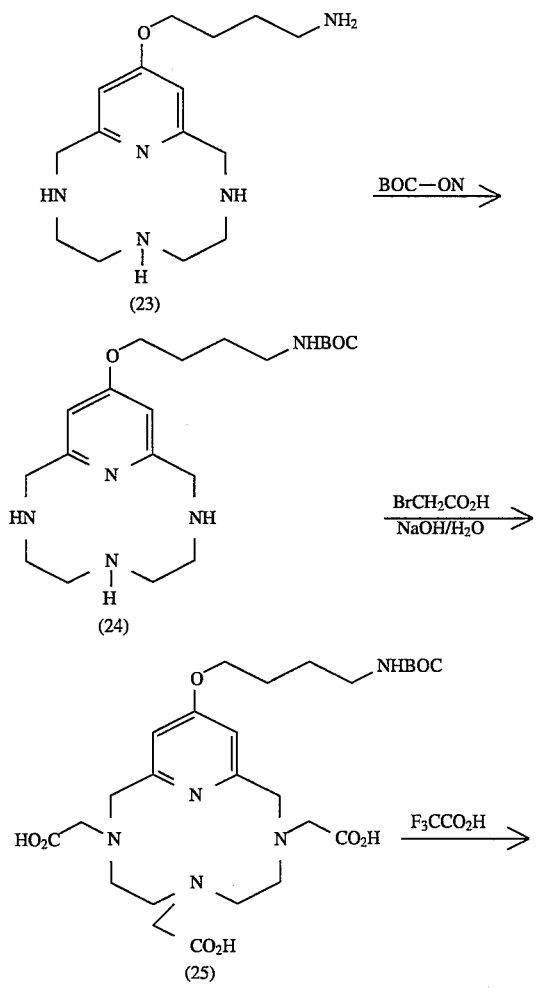
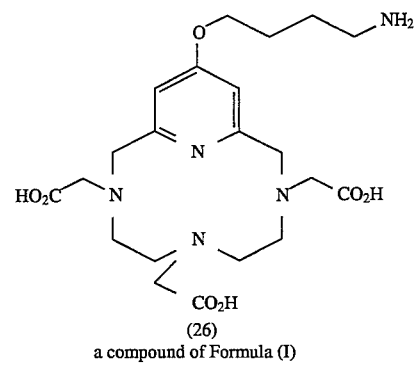
Scheme 5 prepares the compounds of Formula (I) wherein A=CH; and one of Q or Z=CH and the other Q or Z=C—C(O)—R⁶ or C—CH₂—R⁶ where R⁶ is defined as before.
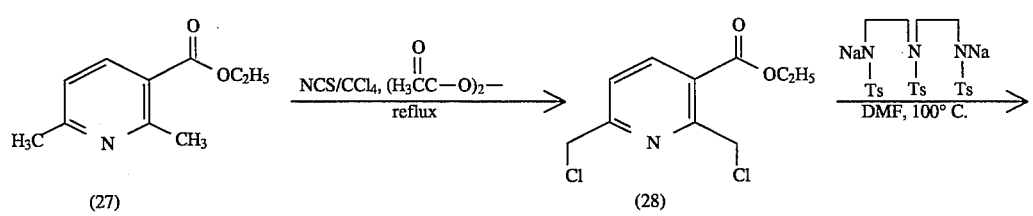
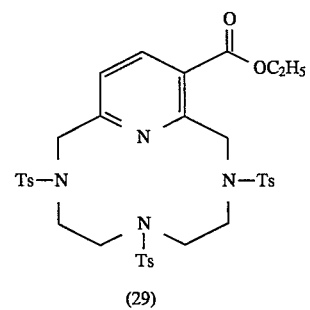

-continued
Scheme 5
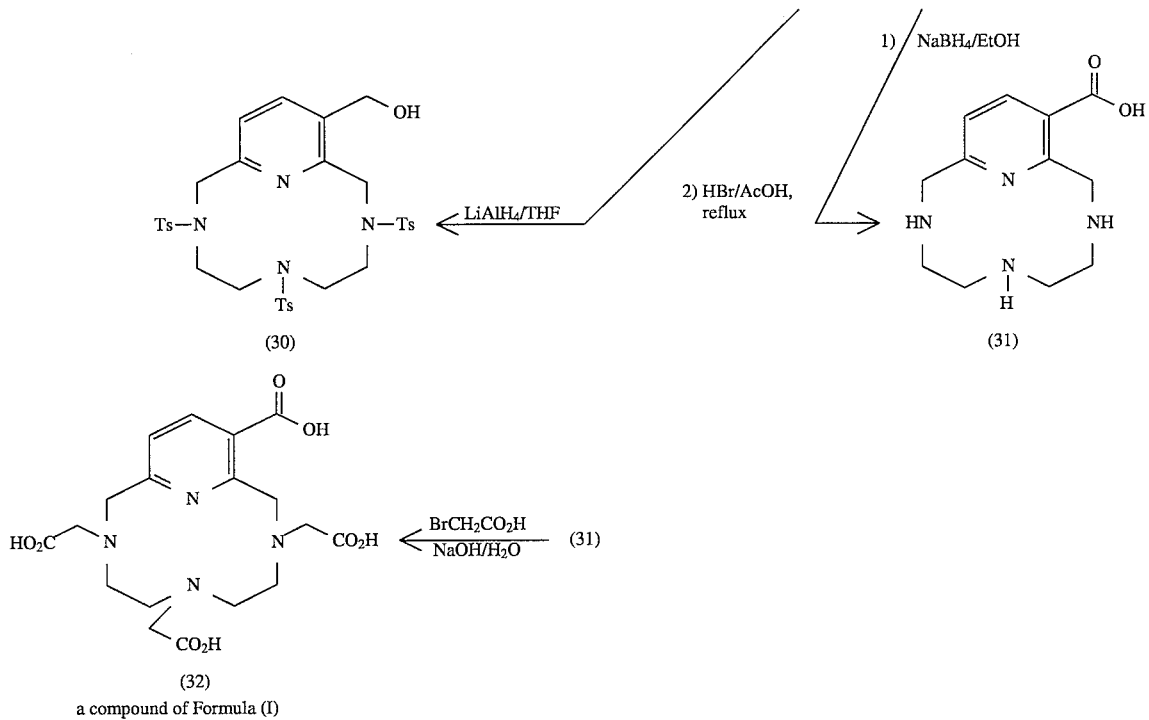
Scheme 6 prepares the compounds of Formula (I) wherein Z=C—CH$_2$—OBz or C—C(O)—R$^5$ where R$^5$=—O—(C$_1$–C$_3$ alkyl), OH or NHR$^6$, where is defined as before; and Q and A=CH.
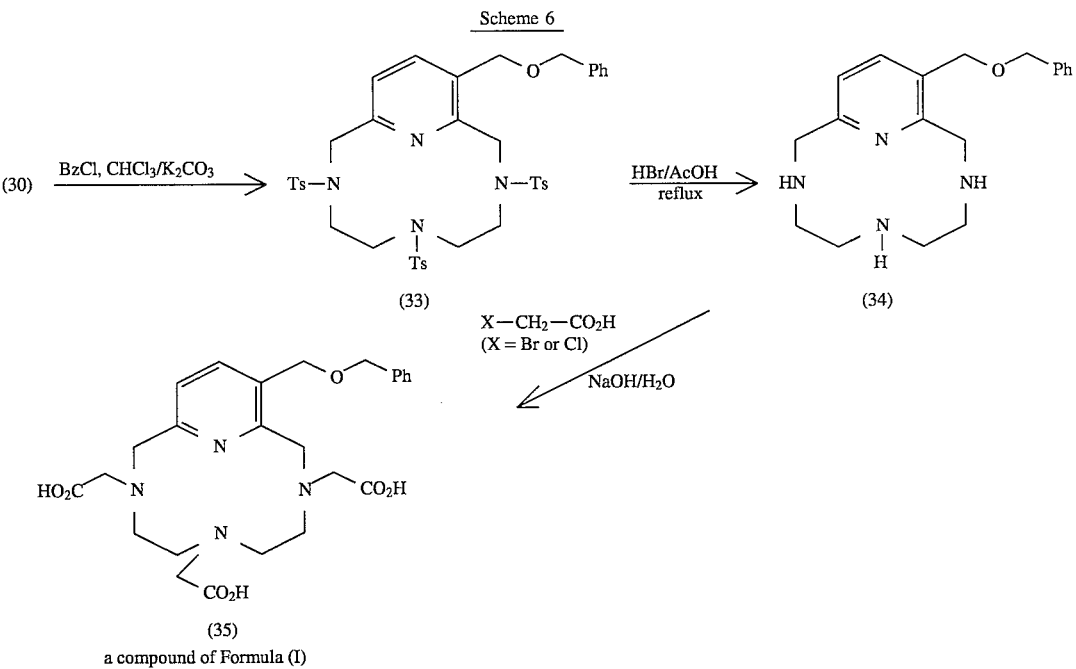

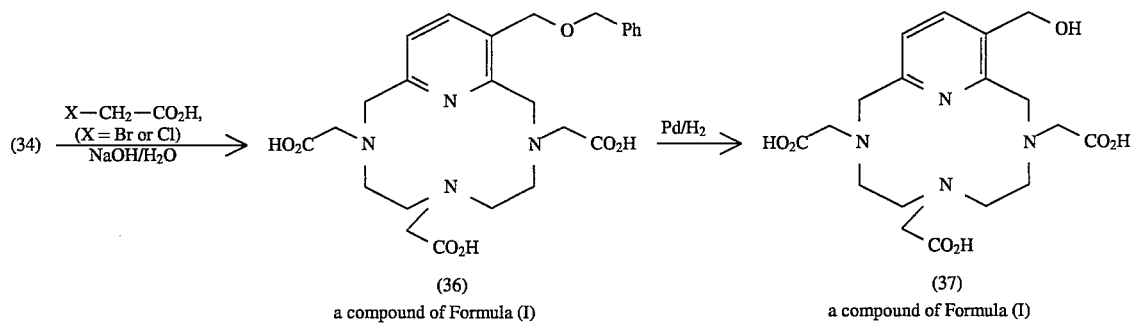
Scheme 7 prepares the compounds of Formula (I) wherein
A=N or $N^+$—$R^5$ $X^-$;
$R^5$=$C_1$–$C_{16}$ alkyl and is $X^-$ halide; and
Q and Z=CH.
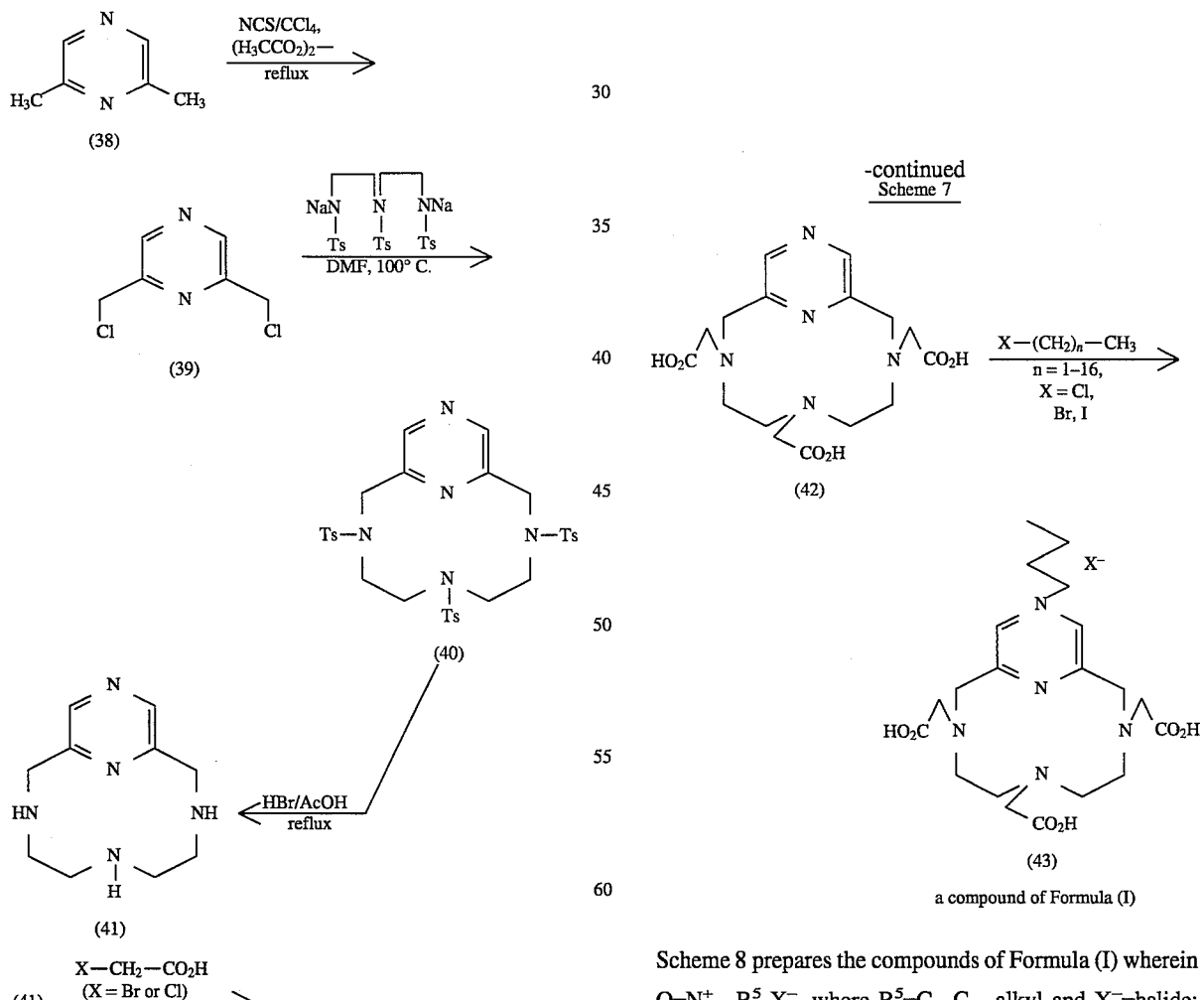
Scheme 8 prepares the compounds of Formula (I) wherein
Q=$N^+$—$R^5$ $X^-$, where $R^5$=$C_1$–$C_{16}$ alkyl and $X^-$=halide; and
A and Z=CH.

Scheme 8
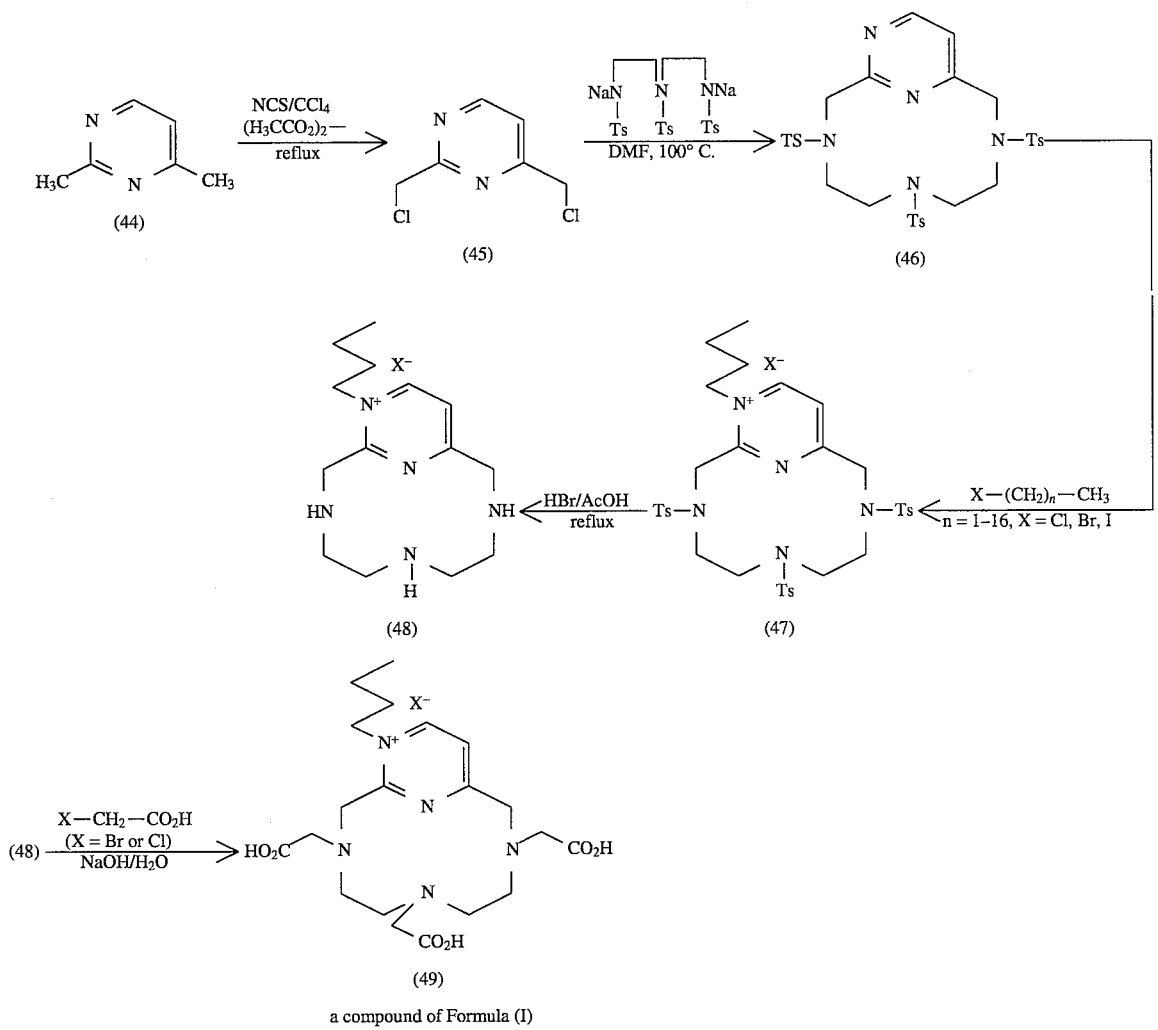
Scheme 9 prepares the compounds of Formula (I) wherein
Q=N or N+—R$^5$ X$^-$, where R$^5$=C$_1$–C$_{16}$ alkyl and X$^-$=halide; and
A and Z=CH.

Scheme 9
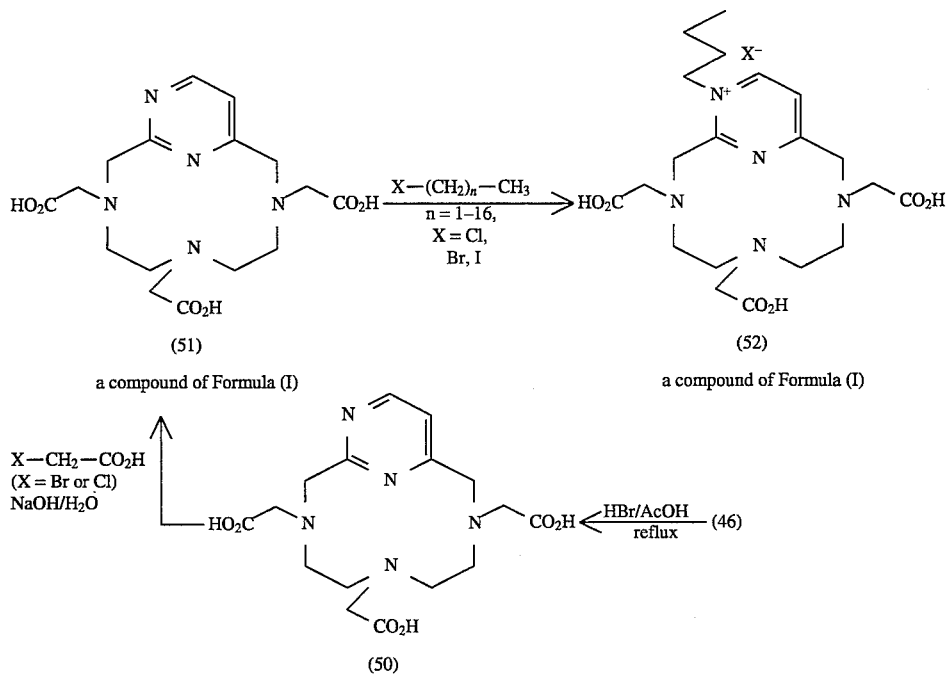
Scheme 10 prepares the compounds of Formula (I) wherein R term at the 6 position is
$$-\underset{Y^2}{\overset{X}{C}}-\!\!\!\!\!\bigcirc\!\!\!-R^4,$$
where
$R^4 = NO_2$ or $NH_2$;
$Y^2 = CO_2H$ (or with a change of reagent $Y^2 = H$); and
A, Q and Z=CH.
Scheme 10
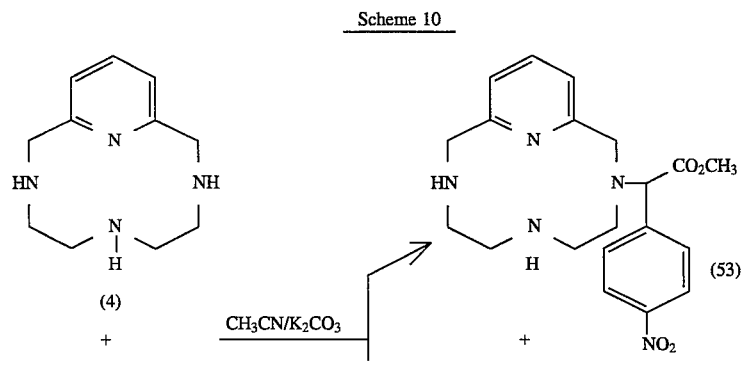

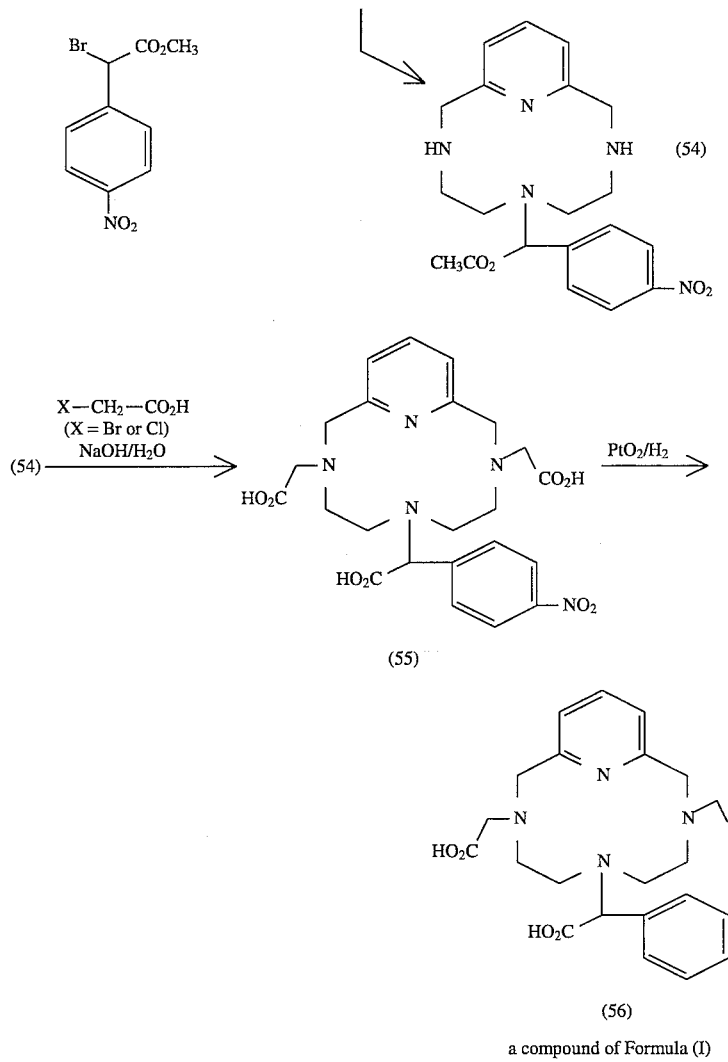
Scheme 11 prepares the compounds of Formula (I) wherein the R term at the 9 position is
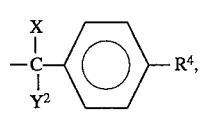
where
R[4]=NO$_2$ or NH$_2$;
Y[2]=CO$_2$H (or with a change of reagent Y[2]=H); and
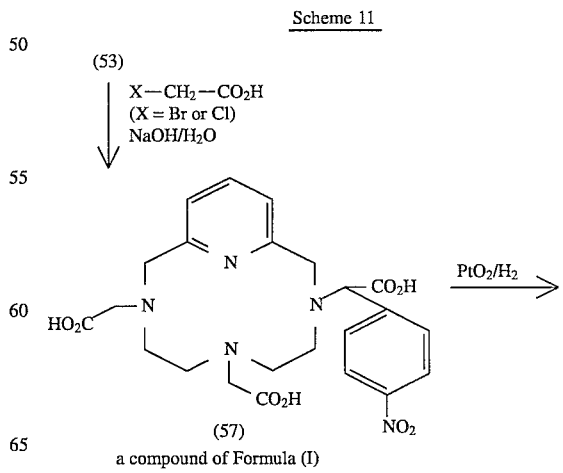

-continued
Scheme 11

(58) a compound of Formula (I)

Scheme 12 prepares the compounds of Formula (I) wherein n=1 (but would also apply if n=2 or 3 with the corresponding change in the reagent), the R term at the 6 position has T=

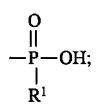

where

R$^1$=—OH; and X and Y=H;

the R term at the 3 and 9 positions have T=COOH;

R$^7$=OH or OCH$_3$; and

A, Q and Z=CH.

Scheme 12

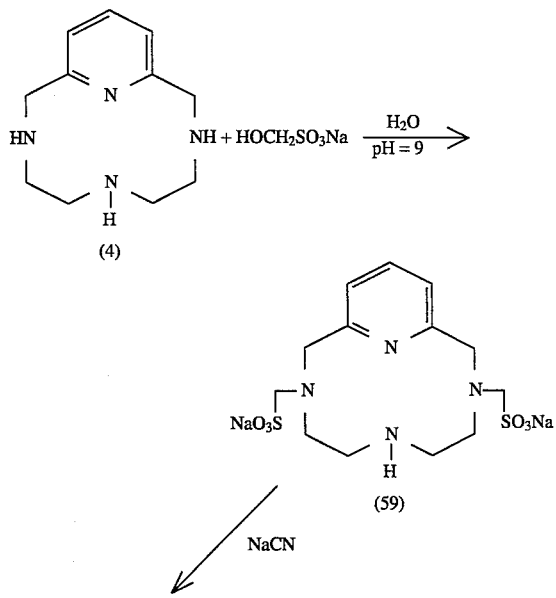

-continued
Scheme 12

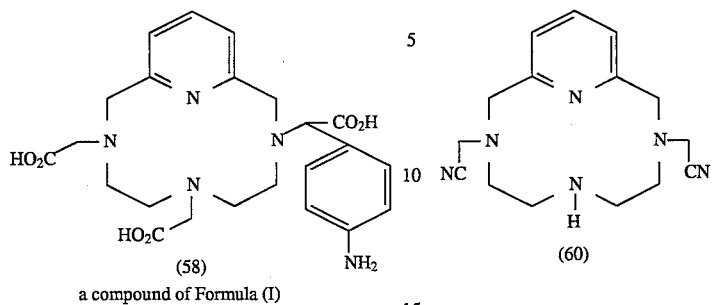

a compound of Formula (I)

In the above Schemes, the general process description illustrates specific steps that may be used to accomplish a desired reaction step. The general description of these process steps follows.

The synthetic Scheme 1 begins with a halogenation of commercially available bis-pyridyl alcohol (1) using thionyl chloride. Similar procedures for converting an alcohol to an electrophilic substrate, such as treatment with toluenesulfonyl chloride, HBr or HCl, should also result in a similarly reactive product which would work well in subsequent ring closure reactions. Macrocyclization procedures are numerous in the literature and the desired tetraazamacrocycle (3) was prepared according to the method of Stetter et al., Tetrahedron 37, 767–772 (1981). More general procedures have since been published which give good yields of similar macrocycles using milder conditions [A. D. Sherry et al., J. Org. Chem. 54, 2990–2992 (1989)]. Detosylation of the intermediate macrocycle [(3) to yield (4)] was accomplished under acidic conditions in good yield. Reductive detosylation procedures are also well known in the literature and can be adapted to the present reaction sequence.

Schemes 10, 11 and 12 delineate a synthetic approach which introduces an aromatic nitrobenzyl substituent at one of the macrocyclic nitrogen positions. Typically, the macrocyclic amine is mono-N-functionalized in an organic solvent such as acetonitrile or DMF at room temperature using a non-nucleophilic base such as potassium carbonate. Additional functionalization of the remaining nitrogen positions is then preformed by methods and conditions described in previous Schemes. After the introduction of the desired chelating moieties, the nitro group is reduced using platinum oxide and hydrogen in water. In this form, the chelating agent is compatible with conjugation techniques which will enable attachment to larger synthetic or natural molecules.

The metal ions used to form the complexes of this invention are $Gd^{+3}$, $Mn^{+2}$, $Fe^+$ and available commercially, e.g. from Aldrich Chemical Company. The anion present is halide, preferably chloride, or salt free (metal oxide).

A "paramagnetic nuclide" of this invention means a metal ion which displays spin angular momentum and/or orbital angular momentum. The two types of momentum combine to give the observed paramagnetic moment in a manner that depends largely on the atoms bearing the unpaired electron and, to a lesser extent, upon the environment of such atoms. The paramagnetic nuclides found to be useful in the practice of the invention are gadolinium ($Gd^{+3}$), iron ($Fe^{+3}$) and manganese ($Mn^{+2}$), with $Gd^+$ being preferred.

The complexes are prepared by methods well known in the art. Thus, for example, see *Chelating Agents and Metal Chelates*, Dwyer & Mellor, Academic Press (1964), Chapter 7. See also methods for making amino acids in *Synthetic Production and Utilization of Amino Acids*, (edited by Kameko, et al.) John Wiley & Sons (1974). An example of the preparation of a complex involves reacting a bicyclo-polyazamacrocyclophosphonic acid with the metal ion under aqueous conditions at a pH from 5 to 7. The complex formed is by a chemical bond and results in a stable paramagnetic nuclide composition, e.g. stable to the disassociation of the paramagnetic nuclide from the ligand.

The complexes of the present invention are administered at a ligand to metal molar ratio of at least about 1:1, preferably from 1:1 to 3:1, more preferably from 1:1 to 1.5:1. A large excess of ligand is undesirable since uncomplexed ligand may be toxic to the animal or may result in cardiac arrest or hypocalcemic convulsions.

The antibodies or antibody fragments which may be used in the conjugates described herein can be prepared by techniques well known in the art. Highly specific monoclonal antibodies can be produced by hybridization techniques well known in the art, see for example, Kohler and Milstein [*Nature*, 256, 495–497 (1975); and *Eur. J. Immunol.*, 6, 511–519 (1976)]. Such antibodies normally have a highly specific reactivity in the antibody targeted conjugates, antibodies directed against any desired antigen or hapten may be used. Preferably the antibodies which are used in the conjugates are monoclonal antibodies, or fragments thereof having high specificity for a desired epitope(s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Some examples of antibodies or antibody fragments are ]1116-NS-19-9, 1116 -NS-3d, 703D4, 704A1, $CC_{49}$, $CC_{83}$ and B72.3. All of these antibodies have been deposited in ATCC. A more complete list of antigens can be found in U.S. Pat. No. 4,193,983, which is incorporated herein by reference. The conjugates of the present invention are particularly preferred for the diagnosis of various cancers.

This invention is used with a physiologically acceptable carrier, excipient or vehicle therefor. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis. The dose will vary depending on the disease and physical parameters of the animal, such as weight. In vivo diagnostics are also contemplated using formulations of this invention.

Other uses of some of the chelants of the present invention may include the removal of undesirable metals (i.e. iron) from the body, attachment to polymeric supports for various purposes, e.g. as diagnostic agents, and removal of metal ion by selective extraction. The ligands of Formula (I) having in at least two R terms T equal to $P(O)R^1OH$ may be used for metal ion control as scale inhibitors. It is likely that these ligands could be used in less than stoichiometric amounts. Similar uses are known for compounds described in U.S. Pat. Nos. 2,609,390; 3,331,773; 3,336,221, and 3,434,969.

The invention will be further clarified by a consideration of the following examples, which are intended to be purely exemplary of the present invention.

Some terms used in the following examples are defined as follows:

LC=liquid chromatrography, purifications were carrier out at low pressure using Dionex 2010i system fitted with a hand-packed Q-Sepharose™ anion exchange column (23×2 cm).

DMF=dimethylformamide.

AcOH=acetic acid.

ICP=inductively coupled plasma.

g=gram(s).

mg=milligrams.

kg=kilogram(s).

mL=milliliter(s).

µL=microliter(s).

pH Stability General Procedure

A stock $^{159}GdCl_3$ solution was prepared by adding 2 µL of $3\times10^{-4}M$ $^{159}GdCl_3$ in 0.1N HCl to 2 mL of a $3\times10^{-4}M$ $GdCl_3$ carrier solution. Appropriate ligand solutions were then prepared in deionized water. The 1:1 ligand/metal complexes were then prepared by combining the ligands (dissolved in 100–500 µL of deionized water) with 2 mL of the stock $159GDCl_3$ solution, followed by through mixing to give an acidic solution (pH=2). The pH of the solution was then raised to 7.0 using 0.1N NaOH. The percent metal as a complex was then determined by passing a sample of the complex solution through a Sephadex™ G-50 column, eluting with 4:1 saline (85% $NaCl/NH_4OH$) and collecting 2×3 mL fractions. The amount of radioactivity in the combined elutions was then compared with that left on the resin (non-complexed metal is retained on the resin). The pH stability profile was generated by adjusting the pH of an aliquet of the complex solution using 1M NaOH or 1M HCl and determining the percent of the metal existing as a complex using the ion exchange method described above.

STARTING MATERIALS

EXAMPLE A

Preparation of 2,6-bis(chloromethyl)pyridine

To 100 mL of thionyl chloride that was cooled {ice bath} was added 24 g (0.17 mol) of 2,6-bis(hydroxymethyl)pyridine. After 30 min, the reaction mixture was warmed to room temperature, then refluxed for 1.5 hrs. After cooling the reaction mixture to room temperature, the solid which formed was filtered, washed with benzene and dried in vacuo. The solid was then neutralized with saturated $NaHCO_3$, filtered and dried to yield 23.1 g (71.5%) of the titled product as an off-white crystalline solid, mp 74.5–75.5° C., and further characterized by:

$^1H$ NMR ($CDCl_3$) δ 4.88 ( s, 4H ), 7.25–7.95 ( m, 3H ).

EXAMPLE B

Preparation of 3,6,9-tris(p-tolylsulfonyl)-3,6,9,15-tetraazabicyclo[9.3.1]pentadeca-1 (15), 11,13-triene A DMF solution (92 mL) of 6.9 g (11.4 mmol) of 1,4,7-tris(p-tolylsulfonyl)diethylenetriamine disodium salt was stirred and heated to 100° C. under nitrogen. To the solution was added dropwise over 45 min 2 g (11.4 mmol) of 2,6-bis(chloromethyl)pyridine (prepared by the procedure of Example A) in 37 mL of DMF. When the addition was completed the reaction mixture was stirred at 40° C. for 12 hrs. To the reaction mixture was then added 50–75 mL of water, resulting in immediate dissolution NaCl, followed by precipitation of the title product. The resulting slurry was then filtered and the solid washed with water and dried in vacuo. The title product was obtained as a light-tan powder, 6.5 g (86%), mp 168°–170° C. dec. and further characterized by:

$^1H$ NMR ($CDCl_3$) δ 2.40 (s, 3H), 2.44 (s, 6H), 2.75 (m, 4H), 3.30 (m, 4H), 4.28 (s, 4H), 7.27 (d, 2H), 7.34 (d, 4H), 7.43 (d, 2H), 7.65 (d, 4H), 7.75 (t, 1H); and 13C NMR δ 21.48, 47.29, 50.37, 54.86, 124.19, 127.00, 127.11, 129.73, 135.04, 135.74, 138.95, 143.42, 143.73, 155.15.

EXAMPLE C

Preparation of 3,6,9,15-tetraazabicyclo{9.3.1}pentadeca- 1(15), 11,13-triene

A solution of HBr and AcOH was prepared by mixing 48% HBr and glacial AcOH in a 64:35 ratio. To 112 mL of the HBr/AcOH mixture was added 5.5 g (8.2 mmol) of 3,6,9-tris(p-tolylsulfonyl)-3,6,9,15 -tetraazabicyclo[9.3.1]pentadeca-1(15),11,13-triene (prepared by the procedure of Example B) and the reaction mixture was heated at mild reflux with constant stirring for 72 hrs. The reaction mixture was then cooled to room temperature and concentrated to approximately 1/10 of the original volume. The remaining solution was stirred vigorously and 15–20 mL of diethyl ether was added. A off-white solid formed which was filtered, washed with diethyl ether, and dried in vacuo. The dry tetrahydrobromide salt was then dissolved in 10 mL of water, adjusted to pH 9.5 with NaOH (50% w/w) and continuously extracted with chloroform for 4 hrs. After drying over anhydrous sodium sulfate, the chloroform was evaporated to give a Light-tan oil which gradually crystallized upon standing at room temperature to yield 1.2 g (71%) of the title product, mp 86°–88° C. and further characterized by:

$^1H$ NMR ($CDCl_3$) δ 2.21 (m, 4H), 2.59 (m, 4H), 3.06 (s, 3H), 3.85 (s, 4H), 6.89 (d, 2H), 7.44 (t, 1H); and $^{13}C$ NMR δ 48.73, 49.01, 53.63, 119.67, 136.29, 159.54.

EXAMPLE D

Preparation of 3,6,9, 15-tetraazabicyclo[9.3.1]pentadeca- 1(15), 11,13-triene-3,6,9-triacetic acid (PCTA)

An aqueous solution (15 mL) of 2.1 g (15 mmol) of bromoacetic acid was added to 0.8 g (3.8 mmol) of 3,6,9, 15-tetraazabicyclo[9.3.1]pentadeca-1(15),11,13-triene (prepared by the procedure of Example C) with stirring at room temperature. After complete dissolution, the reaction mixture was cooled with an ice bath and the pH adjusted to 9 by the slow addition of NaOH (50% w/w). The pH was held constant at 9 throughout 5he reaction by adding small aliquots of NaOH. After 5 hrs the reaction mixture was warmed to 60° C. with continued monitoring of pH. When no further drop in pH could be detected, the reaction was cooled to room temperature and the aqueous solution freeze-dried to give a white solid. The solid was then dissolved in a minimum of hot water and allowed to stand at room temperature for 12 hrs. The resulting crystals were filtered and dried in vacuo to give 1.2 g ( 70% ) of the title product as the trisodium salt, mp 378°–380° C. dec. and further characterized by:

$^1H$ NMR ($D_2O$) δ 2.76 (m, 4H), 3.36 (m, 4H), 3.47 (s, 2H), 4.10 (s, 4H), 7.31 (d, 2H), 7.84 (t, 1H); and $^{13}C$ NMR δ 53.83, 57.31, 57.40, 59.48, 62.36, 125.47, 143.72, 52.67, 172.15, 177.41.

EXAMPLE E

Preparation of 3,6,9,15-tetraazabicyclo[9.3.1]pentadeca- 1(15), 11,13-triene-3,9-dimethylenesulfonic acid A slurry of 500 mg (2.4 mmol) of 3,6,9,15 -tetraazabicyclo[9.3.1]pentadeca-1(15), 11,13-triene (prepared by the procedure of Example C) was stirred in 6 mL of water and the pH adjusted to 3 using 6M HCl. To the mixture was added 682 mg (5.1 mmol) of hydroxymathanesulfonic acid sodium salt and the pH adjusted to 9 with 50 % aqueous sodium hydroxide. After stirring for three hrs at room temperature, $^{13}C$ NMR indicated complete conversion to the title bismethylenesulfonic acid product.

EXAMPLE F

Preparation of 3,6,9,15-tetraazabicyclo[9.3.1]pentadeca- 1(15),11,13-triene-3,9-dimethylenenitrile To the reaction mixture containing 3,6,9,15 -tetraazabicyclo[9.3.1]pentadeca-1(15), 11,13-triene-3,9 -dimethylenesulfonic acid from Example E was added 47 mg (9.6 mmol) of sodium cyanide. The reaction mixture was stirred at room temperature for 24 hrs. $^{13}C$ NMR indicated that transformation to the bis-nitrile was complete. The reaction mixture was then filtered, extracted three×25 mL with chloroform, dried over anhydrous magnesium sulfate, and concentrated to give a viscous oil. The oil was then dissolved in chloroform, triturated with cyclohexane, and concentrated to give, as white powder, 530 mg (78%) of the title dimethylenenitrile product.

EXAMPLE G

Preparation of
3,6,9,15-tetraazabicyclo[9.3.1]pentadeca- 1(15),
11,13-triene-3,9-dimethylenenitrile-6-(2-methoxy-
5-nitrophenyl)methyl acetate To 7 mL of a THF solution of 200 mg (0.73 mmol) of 3,6,9,15-tetraazabicyclo[9.3.1]pentadeca-1(15),11,13 -triene-3,9-dimethylenenitrile (prepared by the procedure of Example F) was added 223 mg (0.73 mmol) of bromo-(2 -methoxy-5-nitrophenyl)methyl acetate. The resulting solution was stirred at room temperature for 12 hrs. To the reaction mixture was added 100 mg of $K_2CO_3$ and the mixture stirred for an additional 2 hrs. The reaction mixture was then filtered and the filtrate concentrated in vacuo. The resulting crude product was then purified by column chromatography (silica gel, 5% $CH_3OH/CHCl_3$).

EXAMPLE H

Preparation of
3,6,9,15-tetraazabicyclo[9.3.1]pentadeca- 1(15),
11,13-triene-3,9-acetic acid-6-(2-methoxy-5
-nitrophenyl)acetic acid 3,6,9, 15-Tetraazabicyclo[9.3.1]pentadeca-1(15), 11,13-triene-3,9-dimethylenenitrile-6-(2-methoxy- 5-nitrophenyl)methyl acetate (prepared by the procedure of Example G) was stirred for 12 hrs at reflux in 6N HCl. The solution was then cooled and concentrated vacuo. The residue was then dissolved in water and lyophilized to give the desired product.

EXAMPLE I

Preparation of 3,9-bis(sodium methylenesulfonate)-
3,6,9,15-tetraazabicyclo[9.3.1]pentadeca-1(15),
11,13 -triene (PC2S)

A solution of 10 mL of an aqueous solution of 1.03 g (5.0 mmol) of 3,6,9,15 -tetraazabicyclo[9.3.11pentadeca-1(15), 11,13-triene (prepared by the procedure of Example C) and 0.5 mL of concentrated HCl was stirred for 10 min at room temperature. The solution had a pH of 8.6. To the solution was then added 1.37 g (10.2 mmol) of $HOCH_2SO3Na$ and 5 mL of deionized water. The solution was then heated at 60° C. for 10 min and the pH was 5.6. After cooling, the pH was adjusted to 9.0 with 1M NaOH, followed by freeze-drying to give the desired product as a white solid (quantitative yield), and further characterized by:

$^1$H NMR ($D_2O$) δ 2.87 (t, 4H), 3.18 (t, 4H), 3.85 (s, 4H), 4.11 (s, 4H), 7.03 (dr 2H), 7.55 (t, 1H); and $^{13}$C NMR ($D_2O$) δ 48.52, 54.04, 58.92, 75.09, 123.90, 141.37, 161.89.

EXAMPLE J

Preparation of 3,9-bis(methylenenitrile)-3,6,9,15
-tetraazabicyclo[9.3.1]pentadeca-1(15),11,13-triene To an aqueous solution of 10 mL of 3,9 -bis(sodium methylenesulfonate)-3,6,9,15 -tetraazabicyclo[9.3.1]pentadeca-1(15),11,13-triene (prepared by the procedure of Example I) was added 10 mL of 0.06 g (12.24 mmol) of NaCN. The reaction mixture was stirred for 3 hrs at room temperature. The solution had a pH of about 10. Upon adjustment of the pH to greater than 13 by with concentrated NaOH, the product precipitated, was extracted with chloroform (3×20 mL), dried over magnesium sulfate, and filtered. Upon removal of the solvent and concentration in vacuo, the desired product was isolated as a waxy white powder, 1.00 g (71%), and further characterized by:

$^1$H NMR ($CDCl_3$) δ 2.03 (s br, 4H), 2.64 (m, 4H), 3.82 (s, 4H), 3.90 (s, 4H), 7.14 (d, 2H), 7.62 (t, 1H); and $^{13}$C NMR ($CDCl_3$) δ 46.64, 52.89, 60.78, 115.31,122.02, 137.57, 157.33.

EXAMPLE K

Preparation of 3,9-diacetic acid-3,6,9,15
-tetraazabicyclo[9.3-1]pentadeca-1(15), 11,13-triene
($PC_2A$)

A concentrated aqueous solution of 30 mL of HCl (37%) and mg (2.5 mmol) of 3,9-bis(methylenenitrile)- 3,6,9,15-tetraazabicyclo[9.3.1]pentadeca-1(15),11,13 -triene (prepared by the procedure of Example J) was heated at reflux for 2 hrs. After cooling, the aqueous solution was evaporated to dryness, followed by coevaporation with deionized water (2×10 mL) to eliminate excess HCl. The pH of the reaction mixture was adjusted to 7 with concentrated NaOH. The resulting nutral solution chromatographed on cation exchange (SP-Sepharose™) column (1.5×50 cm), elutin with first deionized water, then with 1M HCl. The acidic fraction containing product was evaporated to dryness, followed by coevaporation with deionized water (3×10 mL) to eliminate excess HCl. The final product was isolated as a white solid upon freeze drying of the concentrated aqueous solution, and characterized by:

$^1$H NMR ($D_2O$) δ 2.84 (s br, 4H), 3.18 (m, 4H), 3.77 (s, 4H), 4.35 (s, 4H), 7.63 (d, 2H), 8.23 (t, 1H); and $^{13}$C NMR ($D_2O$) δ 47.45, 54.33, 59.73, 60.36, 127.20, 149.31, 155.60, 177.74.

FINAL PRODUCTS

EXAMPLE 1

Preparation of the complex of $^{159}$Gd-3,6,9,15
-tetraazabicyclo[9.3.1]pentadeca-1(15),11,13-triene-
3,6,9-trimethylenecarboxylic acid ($^{159}$Gd-PCTA)

A solution of the ligand of Example D was prepared by dissolving 3.8 mg of ligand/0.517 mL of deionized water (pH=2). A 1:1 ligand/metal complex was then prepared by combining 40 μL of the ligand solution with 2 mL of aqueous $GdCl_3.H_2O$ (3×10$^{-4}$M in 0.01N HCl) containing tracer $^{159}GdCl_3$. After thorough mixing, the percent metal as a complex was determined by passing a sample of the complex solution through a Sephadex™ column, eluting with 4:1 saline (0.85% $NaCl/NH_4OH$), and collecting 2×3 mL fractions. The amount of radioactivity in the combined elutions was then compared with that left on the resin. Under these conditions, complex was removed with the eluent and non-complexed metal is retained on the resin. By this method complexation was determined to be 92%. A sample of the solution that was passed through the resin was used for pH studies. The pH stability was then determined using the General Procedure above.

Complexation for the title product after passing through the resin was determined to be greater than 98% at the 1:1 ligand to metal ratio.

BIODISTRIBUTION

General Procedure

Sprague Dawley rats were allowed to acclimate for five days then injected with 100 µL of the complex solution via a tail vein. The rats weighed between 150 and 200 g at the time of injection. After 30 min. the rats were killed by cervical dislocation and dissected. The amount of radioactivity in each tissue was determined by counting in a NaI scintillation counter coupled to a multichannel analyzer. The counts were compared to the counts in 100 µL standards in order to determine the percentage of the dose in each tissue or organ.

The percent dose in blood was estimated assuming blood to be 7% of the body weight. The percent dose in bone was estimated by multipuling the percent dose in the femur by 25. The percent dose in muscle was estimated assuming muscle to be 43% of the body weight.

In addition to organ biodistribution, chelates of the compounds of Formula (I) were evaluated for efficiency of bone localization since phosphonates are known for their ability to bind to hydroxyapatite.

EXAMPLE I

The percent of the injected dose of complex of of Example 1 ($^{159}$Gd-PCTA) in several tissues are given in Table I. The numbers represent the average of 5 rats? per data point.

TABLE I

| % INJECTED DOSE IN SEVERAL TISSUES FOR Gd-PCTA | |
|---|---|
| Tissue | Average |
| Bone | 7.38 |
| Liver | 0.78 |
| Kidney | 1.81 |
| Spleen | 0.05 |
| Muscle | 7.76 |
| Blood | 5.10 |

The bone to blood ratio (% dose/g) was 7. The bone to liver ratio was 3.5. The bone to muscle ratio was 4.8.

IMAGING EXPERIMENTS

General Procedure

Injectable solutions were first prepared (0.5M) by dissolving the appropriate amount of each complex in 2 mL of deionized water. The pH of the solutions were then adjusted to 7.4 using 1M HCl or NaOH as needed. The total Gd content of each solution was then determined by ICP analysis.

An anethized Sprague Dawley rat was injected intramuscularly with one of the metal solutions described above at a dose of 0.05–0.1 mmol Gd/kg body weight. Images were then taken at various time intervals and compared with a non-injected control at time 0.

EXAMPLE II

The Gd-PCTA complex (prepared in Example 1) was rapidly taken up by the renal system with brilliant enhancement of the kidney cortex as well as peripheral kidney tissue.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:
1. A complex of a bicyclopolyazamacrocyclocarboxylic acid compound of the formula

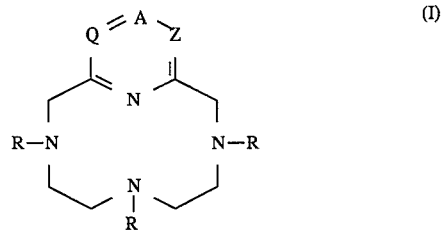

wherein:
R is

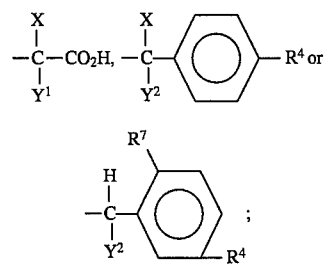

where:
$X$ and $Y^1$ are independently H, OH or $C_1$–$C_3$ alkyl;
$Y^2$ is H or COOH;
$R^7$ is H, OH or $OCH_3$; and
$R^4$ is H, $NO_2$, $NH_2$, isothiocyanato, semicarbazido, thiosemicarbazido, maleimido, bromoacetamido or carboxyl;
with the proviso that at least two R terms must be

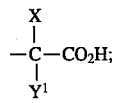

where
$X$ and $Y^1$ are defined as before;
A=CH, N, C—Br, C—Cl, C—$OR\_^1$, C—$OR^2$, $N^+$—$R^3$ $X^-$, or

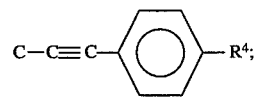

where:
$R^1$=H, $C_1$–$C_5$ alkyl, benzyl, or benzyl substituted with at least one $R^4$:
$R^2$ is $C_1$–$C_{16}$ alkylamino;
$R^3$ is $C_1$–$C_{16}$ alkyl, benzyl, or benzyl substituted with at least one $R^4$;
$R^4$ is defined as before;
$X^-$ is $Cl^-$, $Br^-$, $I^-$ or $H_3CCO_2^-$;
Q and Z independently are CH, N, $N^+$—$R^3$ $X^-$, C—$CH_2$—$OR^1$ or C—C(O)—$R^5$;
$R^1$ and $R^3$ are defined as above:

$R^5$ is —O—($C_1$—$C_3$ alkyl), OH or $NHR^6$;

$R^6$ is $C_1$-$C_5$ alkyl;

$X^-$ is defined as above; and with the proviso that:

a) when Q, A or Z is N or $N^+$—$R^3$ $X^-$, then the other two groups must be CH;

b) when A is C—Br, C—Cl, C—$OR^1$ or C—$OR^2$ then both Q and Z must be CH;

c) the sum of the $R^2$ and $R^4$ terms may not exceed one, and one of $R^2$ or $R^4$ must be present; and d) only one of Q or Z can be C—C(O)—$R^5$ and when one of Q or Z is C—C(O)—$R^5$, then A must be CH; and complexed with a metal ion selected from $Gd^{+3}$, $Mn^{+2}$ or $Fe^{+3}$; or pharmaceutically-acceptable salts thereof.

2. A complex of claim 1 wherein the metal is $Gd^{+3}$.

3. A complex of claim 1 wherein A, Q and Z are CH; and X and Y are H.

4. A complex of claim 1 wherein X and Y are H.

5. A complex of claim 1 wherein A, Q and Z are CH.

6. A complex of claim 1 wherein Q, A and Z are CH; and one R term is

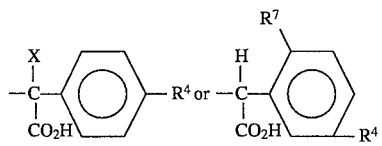

where: X, Y, $R^2$ and $R^4$ are defined as in claim 1.

7. A complex of claim 1 wherein A is C—$OR^1$, C—$OR^2$ where $R^1$ and $R^2$ are defined as in claim 1 or

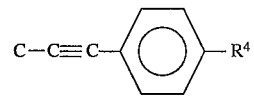

where $R^4$ is defined as in claim 1.

8. A complex of claim 1 wherein A is CH, and one of Q or Z is CH and the other is C—C(O)—$R^5$ or C—$CH_2$—$OR^1$, where $R^1$ and $R^5$ are defined as in claim 1.

9. A complex of claim 8 wherein $R^5$ is $NHR^6$, where $R^6$ is a biologically active material.

10. A complex of claim 1 wherein one of A, Q or Z is $N^+$—$R^3$ $X^-$, where $R^3$ and $X^-$ are defined as above; and the three R terms are

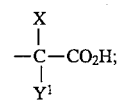

and X and $Y^1$ are all equal to H and the overall charge of the complex is +1.

11. A complex of claim 1 wherein R is

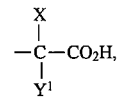

and X and $Y^1$ are all equal to H and the overall charge of the complex is neutral.

* * * * *

UNITED STATES PATENT AND TRADEMARK OFFICE
CERTIFICATE OF CORRECTION

PATENT NO. : 5,480,990
DATED : January 2, 1996
INVENTOR(S) : Garry E. Kiefer and Jaime Simon Page 1 of 2

It is certified that error appears in the above-indentified patent and that said Letters Patent is hereby corrected as shown below:

Column 10, lines 1-29 the formula:

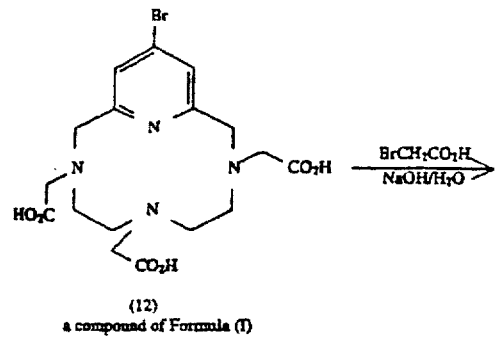

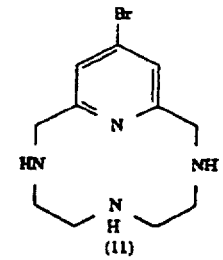

UNITED STATES PATENT AND TRADEMARK OFFICE
CERTIFICATE OF CORRECTION

PATENT NO. : 5,480,990  
DATED : January 2, 1996  
INVENTOR(S) : Garry E. Kiefer and Jaime Simon Page 2 of 2

It is certified that error appears in the above-indentified patent and that said Letters Patent is hereby corrected as shown below:

-continued  
Scheme 2 should read:

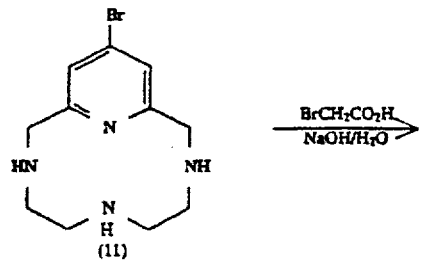

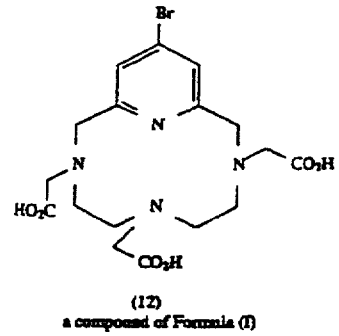

a compound of Formula (I)

Signed and Sealed this

Twenty-first Day of July, 1998

Attest:

BRUCE LEHMAN

Attesting Officer

Commissioner of Patents and Trademarks